(12) United States Patent
Cole et al.

(10) Patent No.: US 12,128,224 B2
(45) Date of Patent: Oct. 29, 2024

(54) AUTOMATIC INTRAVENOUS INJECTION DEVICE

(71) Applicant: THE TRUSTEES OF PRINCETON UNIVERSITY, Princeton, NJ (US)

(72) Inventors: Miles Joseph Cole, Princeton, NJ (US); Craig B. Arnold, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 867 days.

(21) Appl. No.: 17/050,969

(22) PCT Filed: May 6, 2019

(86) PCT No.: PCT/US2019/030828
§ 371 (c)(1),
(2) Date: Oct. 27, 2020

(87) PCT Pub. No.: WO2019/213647
PCT Pub. Date: Nov. 7, 2019

(65) Prior Publication Data
US 2021/0228819 A1    Jul. 29, 2021

Related U.S. Application Data

(60) Provisional application No. 62/667,110, filed on May 4, 2018.

(51) Int. Cl.
*A61M 5/42* (2006.01)
*A61M 5/158* (2006.01)

(52) U.S. Cl.
CPC ............ *A61M 5/427* (2013.01); *A61M 5/158* (2013.01); *A61M 2005/1585* (2013.01);
(Continued)

(58) Field of Classification Search
CPC .................... A61M 5/427; A61M 2005/1585
See application file for complete search history.

(56) References Cited

U.S. PATENT DOCUMENTS 7,946,984 B2 * 5/2011 Brister ................. A61B 5/05
600/347
2006/0129184 A1  6/2006 Peters
(Continued)

FOREIGN PATENT DOCUMENTS

| EP | 3204169 A1 | 9/2017 |
| WO | 0056213 A1 | 9/2000 |
| WO | 2016069936 A1 | 5/2016 |

OTHER PUBLICATIONS

European Search Report for corresponding EP Application No. 19795981, dated Dec. 14, 2021.
(Continued)

*Primary Examiner* — Bradley J Osinski
(74) *Attorney, Agent, or Firm* — MEAGHER EMANUEL LAKS GOLDBERG & LIAO, LLP

(57) ABSTRACT

Disclosed is a portable medical device that can automatically sense the location of a vein and inject a needle to precisely pierce the vein without damaging surrounding tissue. The disclosed device does not require additional assistance for a person to use it on oneself. The disclosed device may optionally employ a basic arm cuff style, and can be used, inter alia, in hospital, military, home infusion, infusion treatment center, emergency response, school, or disaster relief settings.

21 Claims, 5 Drawing Sheets

(52) U.S. Cl.
CPC .................. *A61M 2205/332* (2013.01); *A61M 2205/3576* (2013.01); *A61M 2205/50* (2013.01); *A61M 2205/8206* (2013.01); *A61M 2205/8237* (2013.01)

(56) References Cited

U.S. PATENT DOCUMENTS

| | | |
|---|---|---|
| 2008/0295831 A1 | 12/2008 | Svehaug |
| 2010/0274202 A1 | 10/2010 | Hyde |
| 2012/0190981 A1 | 7/2012 | Harris et al. |
| 2013/0175192 A1 | 7/2013 | Iio et al. |
| 2015/0065916 A1 | 3/2015 | Maguire et al. |
| 2016/0256093 A1 | 9/2016 | Harris et al. |
| 2017/0080166 A1 | 3/2017 | Bagwell et al. |
| 2017/0312474 A1 | 11/2017 | Forde |

OTHER PUBLICATIONS

International Search Report and Written Opinion for PCT/US2019/030828, dated Jul. 17, 2019.
Supplementary European Search Report for corresponding EP Application No. 21784052, dated Feb. 2, 2024.

\* cited by examiner

AUTOMATIC INTRAVENOUS INJECTION DEVICE

CROSS-REFERENCE TO RELATED APPLICATIONS

This application claims benefit of U.S. Provisional Application No. 62/667,110 filed May 4, 2018, which is hereby incorporated in its entirety by reference.

BACKGROUND

In the midst of an evolving technological world, venipuncture for the direct injection of medication has basically not changed since the practice was first developed in the 1830's despite the inefficiency, unreliability, and potential harm that can arise. Under the most ideal conditions it is difficult even for a trained nurse to access a vein consistently due to practical limitations of human motor skills, changing variables from person to person such as vein size, shape, strength, health, etc., as well as basic human error. Of course, under non-ideal conditions, the risks are even greater.

Perhaps the greatest risks are infection caused by large needle punctures, scarring, and other sharps related injuries to both the injectee and the person doing the injection. In fact, the Center for Disease Control and Prevention (CDC) estimates that an average of 1,000 sharps related injuries are sustained by hospital-based healthcare personnel per day nationwide (CDC, 2004). These needle stick injuries result in the transmission of bloodborne viruses and are estimated to cost the healthcare sector in the United States over $3 billion a year. Additionally, according to a new research report by Global Market Insights, bloodborne infections in American hospitals account for around 99,000 deaths per year. Such injuries and infections are 100% avoidable yet despite these challenges, millions of Americans require IV injections every day for a wide range of infusion therapy treatments and a large percentage of these require the person themselves or another, untrained assistant to perform the venipuncture.

Two particularly important spaces where an automatic IV detection and insertion device would revolutionize the market space are hemophilia and chemotherapy. Hemophiliacs require daily IV injections, and either a trained nurse must come to your house, you must travel to a treatment center, or you must do the injection yourself. Even in a hospital setting, around 25% of first stick IV infusion attempts are unsuccessful illustrating the difficulty of injecting a vein in small or weakened patients. Hemophiliacs, cancer patients, and patients with diseases treated by IV infusions must go through the mentally and physically taxing process of learning to self-infuse as does their family, especially in the case of children. It is inconceivable that in this age of advanced technology we rely on such outdated and inefficient methods.

As such, an easy-to-use system capable of providing accurate intravenous injection while removing the risk of human error is useful and desirable.

BRIEF SUMMARY

Disclosed is a device for automatically injecting a needle vertically into a user's vein. The device includes a clamp mount for securing a needle, sensors to detect and identify the position of a vein, motors to maneuver the clamp mount laterally, and to vertically inject the needle into a vein, a force sensor to determine when the needle has pierced the vein, and a processor to control the device.

The vein identification sensor may be based on optical inspection, ultrasound, thermal imaging, or proximity sensors. The motors may be linear or piezoelectric motors. The device may include a tube connecting the needle to a syringe. The needles may be a 32-gauge 4 mm needle, a 27-gauge 12.7 mm needle, a 26-gauge 12.7 mm needle, or a 25-gauge 15.9 mm needle. The device may advantageously also include a vein identifying light, a thermal imaging sensor for verifying the injection point is suitable for injection, and/or a vein rolling prevention bar, which may be between 0.5 cm and 2.5 cm long.

The device may also advantageously include a cuff, where the clamp mount, sensors, and motors are contained on or within the cuff, and wherein the cuff is capable of being in direct contact with a patient's body. The cuff may be designed to fit on an arm or a leg. The device may contain a battery and may contain an electrical connector to recharge the battery. The device may contain a wireless transmitter. The device may contain one or more buttons, such as a stop button and an eject button.

DETAILED DESCRIPTION

The device disclosed herein solves the problems associated with human error during intravenous injections. By precisely and automatically injecting a needle into a vein, the disclosed device will prove to be very cost efficient for hospitals, insurance companies, the federal government, and private users alike.

Disclosed is an automatic intravenous injection device. More particularly, disclosed is a portable medical device that can automatically sense the location of a vein and inject a needle to precisely pierce the vein without damaging surrounding tissue. The disclosed device does not require additional assistance for a person to use it on oneself. The disclosed device employs a basic arm cuff style, and can be used, inter alia, in hospital, military, home infusion, infusion treatment center, veterinary, emergency response, school, or disaster relief settings.

An important use of the disclosed device is to inject a needle into a vein for the purpose of infusing medication intravenously. However, the disclosed device has other uses such as injecting a needle for drawing blood (e.g., using a device configured to allow a blood collection tube to be inserted and removed), dialysis (e.g., using two devices, one for drawing blood for a dialysis machine, and one for returning the blood to the subject), tissue biopsy (e.g., using an appropriate needle for the biopsy), or other medical procedures, and can also be used with non-human subjects, such as in certain veterinarian applications.

The disclosed device employs a vertical injection technology (VIT). In short, this approach injects a needle at a 90-degree angle from the surface of the skin, in contrast to the typical 45-degree (or other) angle that a doctor or nurse might use. Furthermore, the disclosed device employs a delicate force sensor to determine the location of the needle relative to the body at all times and, in particular, to accurately determine the exact moment when the vein is pierced.

Figure 1:
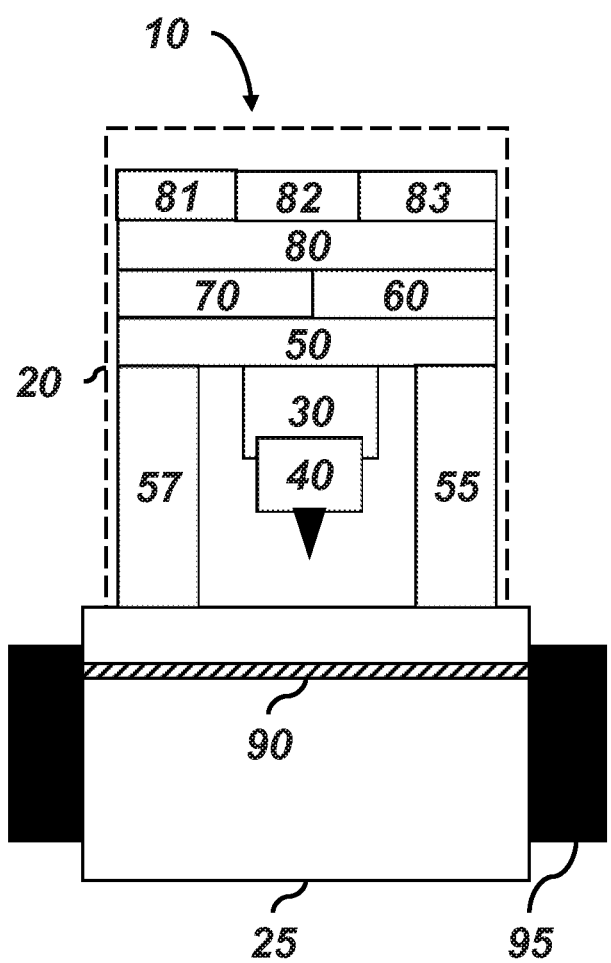
FIG. 1 is a schematic of one embodiment of a disclosed device.

Referring to FIG. 1, the disclosed device (10) contains multiple components. The device (10) generally consists of a clamp mount (30) for securing a needle (40). In various embodiments, the mount is configured to receive and secure commercially available 32-gauge 4 mm needles, 27-gauge 12.7 mm needles, 26-gauge 12.7 mm needles, and/or 25-gauge 15.9 mm needles. In certain embodiments, the needle is a custom needle. In certain embodiments, the clamp mount is configured to secure a syringe. In certain embodiments, the needle is operably connected to a flexible tube, which is operably connected to a syringe or other mechanism for providing a liquid medication to the needle for injection. In some embodiments, the mount also comprises gearing or motors designed to move the clamp in and out of the device, like the tray of a CD-ROM drive, so as to allow a user easier access to the clamp. In some embodiments, the system also includes a sensor to detect the presence of a needle.

The system (10) also includes at least one sensor (60) to allow the detection and identification of a position of a vein (90), including but not limited to a vein within a user's arm or leg (95).

In certain embodiments, the sensor used to detect and identify the location of the vein is based on optical inspection (e.g., using a visual light or IR detectors), ultrasound, or thermal imaging, or proximity sensor.

In a preferred embodiment, infrared optical technology is used to identify the location of a vein. This technology has been proven accurate at creating high resolution 2-D maps of veins and can be easily implemented by one of skill in the art with diode illumination and standard off-the-shelf-detectors. For example, irradiating an area with infrared light allows an image to be captured showing the differential absorption and reflection of the light by subcutaneous veins and surrounding tissue. However, these approaches are known to be somewhat limited in their ability to measure depth. Thus, the positioning sensor(s) (60) are not used to measure depth, but rather simply for their ability to allow the device to generate a 2-D location of a vein (90).

The system (10) also includes one or more motors (50, 55, 57) configured to move the clamp mount laterally to a location above skin at the position of the identified vein, and further configured to inject the needle vertically into the skin at the position of the vein. The systems to move the clamp mount may utilize, e.g., linear motors, piezoelectric motors, worm drives, gears, and/or belts.

In one embodiment, the one or more motors (50, 55, 57) comprises 6 linear motors—2 linear motors (e.g., 50) to maneuver the clamp mount (30) and needle (40) laterally above the skin to get the needle positioned above a vein, and 4 linear motors (e.g., 55, 57) to maneuver the clamp mount (30) and needle (40) up and down, eventually injecting the needle (40) into a vein (90). In certain embodiments, the clamp mount (30) is connected to the two lateral linear motors (50), which in turn are connected to either the front (57) or back (55) vertical linear motors. In one embodiment, the four vertical motors surround the clamp mount, with the two lateral motors attached between the front and back left, and front and back right vertical motors.

In another embodiment, the one or more motors (50, 55, 57) comprises three motors-a single lateral motor (50) and two vertical motor (55 and 57). In another embodiment, the one or more motors (50, 55, 57) comprises just two motors-a single lateral motor (50) and a single vertical motor (55 or 57).

At least one sensor (70) is utilized to determine when the needle (40) has pierced the vein (90). In preferred embodiments, the sensor (70) is a force sensor.

In some embodiments, as the motors that vertically lower the clamp and needle towards the target insertion site, the resistance of the needle as it enters and passes through various features (skin, fat, muscle, vein, etc.) is measured by the sensor(s) (70). For example, as the needle (40) is lowered, these force sensors detect the difference in friction between the needle pressing through skin tissue vs. when the needle enters into the liquid (blood) of the vein. When the sensor(s) (70) detect a difference in resistance that suggests that the needle has entered the vein, the system sends a signal to the stop the downward movement of the clamp mount (30). The difference in resistance can be calibrated for intact skin, scar tissue, fat, muscle, etc., based on the particular needle being utilized.

In preferred embodiments, the force sensor has a frequency of less than 100 ms. To determine whether the needle has entered a vein, the system considers at least the change in force from one measurement to the next and optionally also the absolute value of the force itself. If the considered values are within a predetermined range, a vein has been entered. In other embodiments, the trends in the considered values are tracked over a period of time to determine if a vein has been entered. For example, if the period of time being considered is the entirety of the injection, then during an injection, the needle must first pierce the dermis, then move through the epidermis, enter the subcutaneous tissue, and finally enter a vein. In this example, each of those different transition points may have a range for the change in force associated with the transition, and if the processor does not detect a change in force that matches the expected ranges of all the expected transitions, it will not make a determination that a vein has been entered.

For the entirety of the infusion, the sensor(s) (70) detect and adapt in real time to the changing position of the vein. For example, if the vein rises up a millimeter, the force sensors can recognize this and send a signal to the motors to also move the needle up a millimeter.

Additionally, the force measurement allows the system to determine if a vein is even hit, or if the vein has collapsed (rendering the injection impossible). For example, if the force sensor does not detect a force measurement, or a change in force measurement, that would indicate a vein has been entered, and the linear motor has travelled at least a particular distance (4 mm, In other embodiments, the system utilizes a sensor that determines when the needle has pierced the vein is based on back flow of blood into the needle. For example, an optical sensor can detect the presence of blood in a clear tube operably connected to the needle, or a pressure sensor can detect a change in an operably connected tube when blood has entered the tube.

Figure 2:
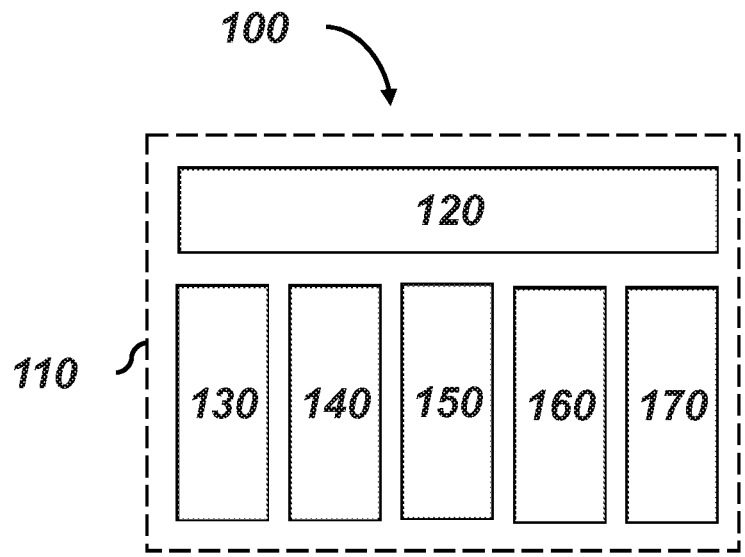
FIG. 2 is a schematic of one embodiment of a single board computer that may be used in the device.

The system also includes a microprocessor (80) configured to automatically control the needle injection process. Referring to FIG. 2, in preferred embodiments, the microprocessor (80) is a part of a single board computer (SBC) (100). The SBC (100) may include a board (110) the contains the processor (120), storage (130) which may include RAM, ROM, or some combination thereof, drive controls (140) for at least the various motors, at least one A-D converter (150), digital input/output (160) and an interface (170). The interface (170) may include a wired or wireless connection to allow data collected during injection to be reported. In some embodiments, this is a Bluetooth connection to a mobile device, a wireless connection over a WiFi network, or through an ethernet connection. In other embodiments, the device can communicate with a pump or valve—when the device detects it has entered a vein, the device sends a signal indicating the pump can turn on (or the valve can open), and the medication can be provided automatically.

The system (10) may also include additional components.

As shown in FIG. 1, a first additional component is a housing (20) for the various components described above. Generally, this housing will include a small opening for insertion of the needle but will otherwise generally protect the components from the environment. In some embodiments, a small door is provided, that is closed when no needle is in the clamp mount, but the door can open to allow access to the clamp.

Figure 3:
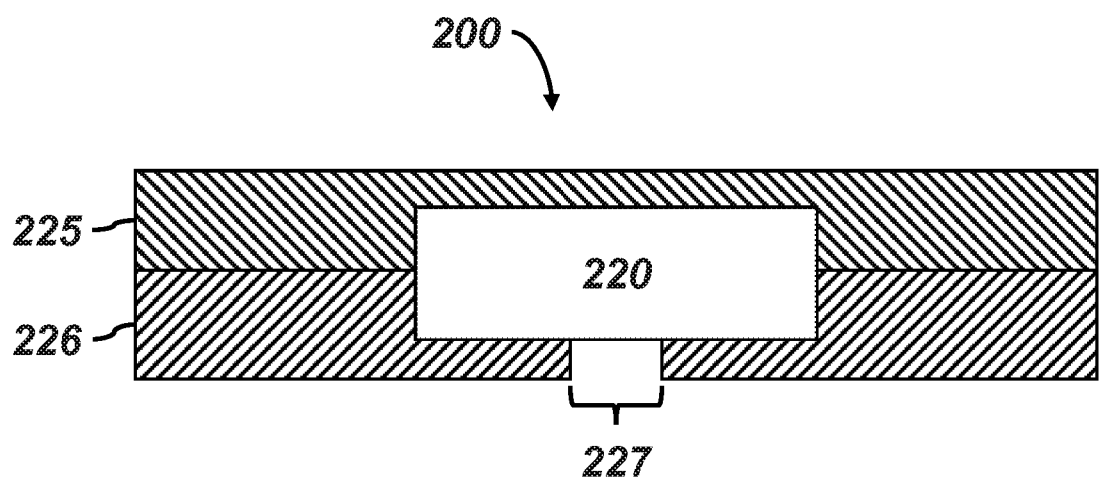
FIG. 3 is a side-view of one embodiment of a disclosed device.

As shown in FIG. 1, a second additional component is a cuff (25). The housing (20) is generally attached to the cuff (25). In some embodiments, at least the clamp mount, sensors, and motors are contained on (e.g., as shown in FIG. 1, contained within a housing, the housing being secured or attached onto an outer surface of the cuff) or within the cuff. An example of a system (200) with those components being within the cuff is shown in FIG. 3, which shows a side-view of an embodiment. There, the housing (220) is between a top layer of the cuff (225) and a bottom layer of the cuff (226). Typically, there may be one or more openings (227) in the top or bottom layer of the cuff for, e.g., allowing access to the clamp mount, or allowing the needle access to the skin.

Figure 4:
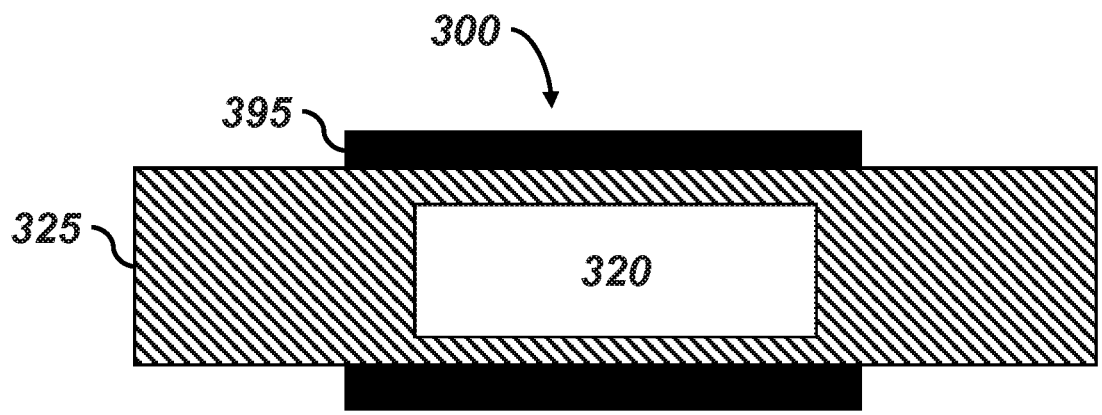
FIGS. 4 and 5 are top-down views of embodiments of disclosed devices.
Figure 5:
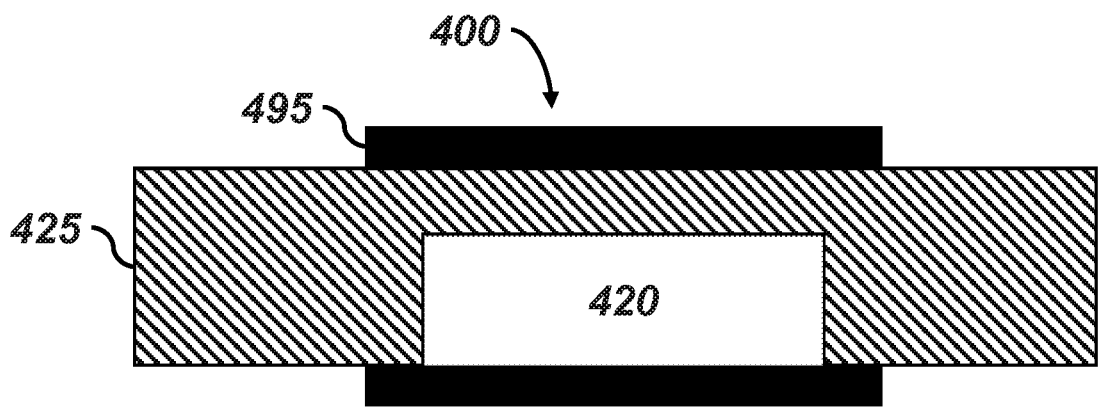

While there are no restrictions on the dimensions of the cuff or placement of the components on or near the cuff, in certain embodiments (see FIG. 4), the cuff (325) and housing (320) are arranged such that the housing is roughly centered forward-to-backward on the cuff (arm 395 is shown for reference as to how the device would be worn). In other embodiments (see FIG. 5), the cuff (425) and (420) are arranged such that the housing is lined up on or near one of the edges of the cuff (arm 495 is shown for reference as to how the device would be worn). This approach may allow easier access to the clamp and make it easier for a user to position the device on an arm or leg.

The cuff should be a woven or nonwoven material flexible and pliant enough to fit various user's arms and/or legs. In some embodiments, the cuff is a stretchable material. In other embodiments, the cuff can be wrapped around an arm or leg, similar to how an upper arm blood pressure cuff operates. Note that in some embodiments, no cuff is present. In some embodiments, a user can simply place, or adhere, the housing into place on an arm, leg, etc.

In some embodiments, the cuff is inflatable. For example, the cuff may have a hard, outer shell with rubber inflatable tubing on the inside, large enough to encompass arms or legs of, e.g., a typical human being. The rubber tubing may remain deflated while the cuff is slid into position. Once device is in position, tubing is then automatically or manually inflated until device is tightly secured in place. This tubing's constriction on the arm may also be configured to act as a tourniquet and also prevents the target vein from rolling. In some embodiments, an inflation pump is used, that works by squeezing. The pump is operably connected to the tube, and by squeezing multiple times, air is pushed into the tubing to make the cuff tighter on the user's appendage.

Although not shown in FIG. 1, a third additional component is a vein rolling prevention bar. This is typically a small (e.g., 0.5 cm×0.5 cm×2.5 cm) relatively inflexible bar that is configured to lower onto the skin above and further up the arm from the injection site in order to prevent the targeted vein from rolling.

Embodiments utilizing this feature will likely have the rolling prevention bar connected to the vertical linear motors. In some embodiments, after the vein identification sensors identify a vein, the vertical motors lower the bar sufficient to prevent the target vein from rolling. The vein identification sensors may then reassess the target area, make any lateral adjustment needed, ahead of allowing the vertical motors to inject the needle. In some embodiments, following completion of an infusion, or at the press of a button, the rolling prevention bar may be raised back to its starting position.

As shown in FIG. 1, a fourth additional component is a battery or other portable power source (81). In some embodiments, the system contains a rechargeable battery sufficient to power the device for at least, e.g., 7 injections. In some embodiments, the system also includes an electrical connector to recharge the battery, and/or a wireless coil for recharging the battery by RF transmission.

As shown in FIG. 1, a fifth additional component is a thermal imaging sensor (82). The thermal imaging sensor is a small infrared imaging device used to verify that the vein is suitable for injection by assessing that it has a healthy blood flow by distinguishing the vein temperature difference compared to the rest of the arm. Typically, this will be positioned directly above the clamp mount, looking vertically down onto the target vein insertion site area. In operation, this sensor may use thermal infrared imaging to assess the difference in temperature on the user's forearm in order to roughly estimate the location of the vein. This is what is used to distinguish a suitable vein from, e.g., a freckle. Once this rough estimation of the location of the vein is established, the system sends this information to the other sensors, so they know where to look in order to determine a more exact estimation of the vein location.

As shown in FIG. 1, a sixth additional component is one or more indicators and/or buttons (83). In some embodiments, the buttons may include a green start button, an red stop button (e.g., stopping any injection, raising the needle out of the body, etc.) and/or an eject button (e.g., ejecting the needle from the clamping mount). In some embodiments, the indicators may include a battery life indicator, or status LEDs.

Although not shown in FIG. 1, a seventh additional component is a vein identifying light (81), such as that used by the Accuvein® AV400 vein illuminator. Other light-based vein locator techniques known to those of skill in the art include those employed by the Veinlite® LED+® vein illuminator, and the Vein Viewer® Flex vein illuminator.

Such lights can be shined onto a user's skin to make it easier to see veins that are not clearly visible on the surface. In preferred embodiments, these vein identifying lights would typically be attached to an outside wall of the housing, looking down towards the skin. In this fashion, it could be used to help the user identify a good target vein. The user could shine this light on their arm, and then place the cuff as close as possible to a potential vein made visible by this light.

Figure 6:
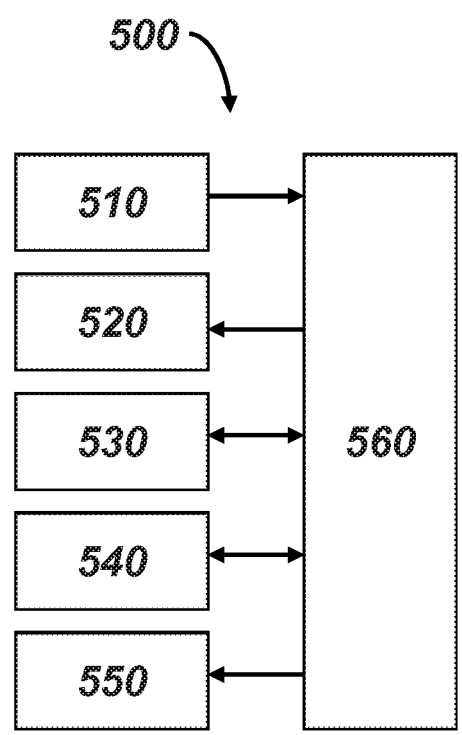
FIG. 6 is a schematic indicating an embodiment of how various devices are controlled.

Referring to FIG. 6, some embodiments of the device are configured such that the processor controls the functioning of the device. In the system (500) of FIG. 6, the processor (560) receives input from various user interfaces (510), such as buttons, touch screens on mobile devices, etc. The processor may also send data and/or other output to various displays or other indicators (520), which may include mobile devices, LEDs, LCD displays, etc. The vein locating sensors (530) typically receive control signals from the processor and send data back to the processor. Similarly, the sensors for detecting when the needle has been properly inserted into a vein (540) also receive control signals from the processor and send data back to the processor. And finally, the motor controls (550) tend to only receive control instructions from the processor (580).

Figure 7:
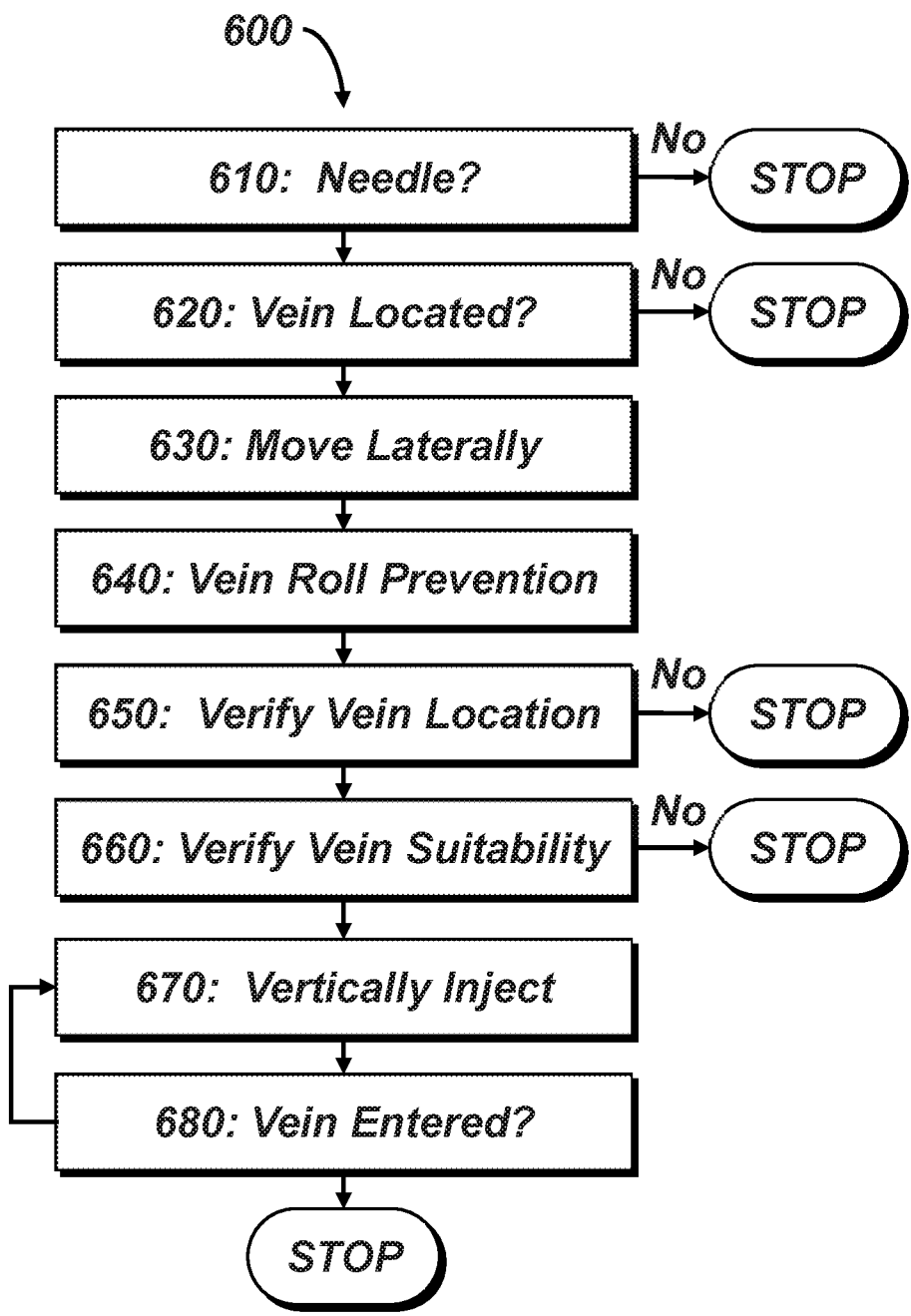
FIG. 7 is a flowchart of one method for utilizing the disclosed device.

One example of a method can be seen with reference to FIG. 7. In the method (600), the system first determines if a new needle has been inserted (610). In some embodiments, the processor increments a flag by 1 when a needle is first inserted, increments the flag again by 1 when the injection sequence ends, and only resets the flag when the needle-detecting sensor no longer detects the presence of a needle. So, if the flag-0, no needle has been inserted, and if the flag>1, a previously-used needle was not removed. If this is the case, the system may be configured to either not proceed further, provide a warning of the issue or other indicator to the user, and/or allow a user to override the system and proceed.

If a needle is present, the vein identification and location system is activated (620). If the system does not detect and location the position of a vein, the system stops and/or sends a warning or other indicator of a problem to the user. In some embodiments, this may involve taking a highly contrasted image of the skin under IR light, identifying the center of a sufficiently large group of dark pixels, and counting pixels to identify the center of a vein.

Once a vein is detected and located, the system may then move the needle laterally (630) until it is over the vein.

The system may then utilize its vein rolling prevention bar to prevent vein rolling (640), after which the system may verify the positioning of the vein (650) and that the vein is suitable for injection (e.g., via a thermal imaging sensor) (660).

The system may then begin the iterative process of vertically injecting the needle into the skin and measuring force (670) and determining if a vein has been entered (680). If a vein is entered, the process may stop, provide a warning/indication to a user that a vein has been entered, and/or send a signal to an external device indicating it may begin, e.g., injecting medication, etc. If a vein is not entered, the system may either continue the interactive process, or it may stop and indicate the system has failed to enter into a vein. For example, the system may determine that if a vein has not been reached in a set period of time, or after the needle has moved a certain vertical distance, something unexpected happened and an error has occurred. In these situations, the system may send a warning/indication of the error.

The disclosed device has a method of identifying the location of the vein and manipulating the location of the needle. The design of the disclosed device uses a basic arm cuff style which further distinguishes it from prior systems that rely on large, fixed robotic devices and machines to both sense the vein location and inject the needle at a desired angle.

One embodiment requires a user to first attach a syringe with the desired medication to tubing with a 32 gauge, 4 mm needle. Then, the user assesses their arm for the most visually prominent veins. If no veins are clearly visible, a vein identification light may be used to determine a good insertion site. Once the user has identified a good insertion site, the user swabs area with a sterile alcohol pad. The disclosed device is then placed over your swabbed target vein, preferably aligning the middle of the clamping mount as close to directly above the target vein as possible. The device is then secured in place by wrapping the cuff around the user's forearm and tightly connecting, e.g., Velcro® hook-and-loop fasteners on the ends of the cuff. Then, the user inserts the 4 mm needle into the clamping mount. In certain embodiments, the user may then click the green start button (alternatively, the user may press a start button on a smartphone app, etc.). The device will then detect and identify a vein. The clamping mount will be lowered, and the needle will be inserted vertically into the vein. The user may see blood flow back into the tubing if the vein is successfully accessed. If the user sees this blood, the user may then infuse the medication the user normally would, at their own pace. When the user is finished, the user may press the red stop button and the clamping mount will be raised and the needle will be removed from the vein. A user may then click the needle eject button to eject the needle from the clamp. The cuff may then be removed, and the needle disposed of.

Benefits of the disclosed device include that it is small, portable, safe, able to be used by a single or untrained individual, and others. The disclosed device solves the problem of inaccurate and unsuccessful needle injections by giving users a system that automatically finds and injects a vein.

The disclosed device has a number of potential commercial applications. The disclosed device can be useful in hospital, military, veterinary, home infusion, infusion treatment center, emergency response, school, or disaster relief settings. The disclosed device is portable, and a patient can use the device on themselves without the assistance of a certified care physician. No known technologies are easily portable or created for self-use.

What is claimed is:

1. An injection device for automatically injecting a needle vertically into a user's vein, comprising:
    a clamp mount for securing a needle;
    a sensor configured to detect a 2D position of a vein, and is not configured to determine a depth of the vein;
    one or more motors configured to move the clamp mount laterally to a location above skin at the 2D position of the vein, and further configured to inject the needle vertically into the skin at the 2D position of the vein;
    a force sensor to determine when the needle has pierced the vein; and
    a microprocessor configured to generate a 2D location of the vein based on data from the sensor and automatically control injection of the needle.

2. The injection device of claim 1 in which the sensor to detect the location of the vein is based on optical inspection.

3. The injection device of claim 1 in which the sensor to detect the location of the vein is based on ultrasound.

4. The injection device of claim 1 in which the sensor to detect the location of the vein is based on thermal imaging.

5. The injection device of claim 1 in which the sensor to detect the location of the vein is based on proximity sensors.

6. The injection device of claim 1, wherein the one or more motors comprises a linear motor.

7. The injection device of claim 1, wherein the one or more motors comprises a piezoelectric motor.

8. The injection device of claim 1, further comprising a tube attached to the needle and a syringe attached to the tube.

9. The injection device of claim 1, wherein the needle is a 32-gauge 4 mm needle, a 27-gauge 12.7 mm needle, a 26-gauge 12.7 mm needle, or a 25-gauge 15.9 mm needle.

10. The injection device of claim 1, further comprising a vein identifying light.

11. The injection device of claim 1, further comprising a thermal imaging sensor for verifying an injection point is suitable for injection.

12. The injection device of claim 1, further comprising a vein rolling prevention bar.

13. The injection device of claim 12, wherein the vein rolling prevention bar is about 0.5 cm to 2.5 cm long.

14. The injection device of claim 1, further comprising a cuff, wherein the clamp mount, sensors, and motors are contained on or within the cuff, and wherein the cuff is capable of being in direct contact with a patient's body.

15. The injection device of claim 14, wherein the cuff is designed to fit on an arm or a leg.

16. The injection device of claim 1, further comprising a battery to power at least one electronic component, where the at least one electronic component is the sensor, the one or more motors, the force sensor, and/or the microprocessor.

17. The injection device of claim 16, further comprising an electrical connector to recharge the battery.

18. The injection device of claim 1, further comprising a wireless transmitter operably connected to the microprocessor to report data collected during injection.

19. The injection device of claim 1, further comprising a wired or wireless communication interface.

20. The injection device of claim 1, further comprising an automatic stop button and/or an eject button.

21. The injection device of claim 1, wherein injecting the needle into the skin consists of moving the needle vertically.

* * * * *